United States Patent [19]

Carr et al.

[11] Patent Number: 5,426,231

[45] Date of Patent: Jun. 20, 1995

[54] PROCESS FOR PRODUCING AMINOPROPANOLS

[75] Inventors: Richard V. C. Carr, Allentown; Barry J. Koehler, Mertztown, both of Pa.

[73] Assignee: Air Products and Chemicals, Inc., Allentown, Pa.

[21] Appl. No.: 177,499

[22] Filed: Jan. 5, 1994

[51] Int. Cl.$^6$ ............................................. C07C 209/48
[52] U.S. Cl. ..................................... 564/493; 558/391; 558/446; 564/259; 564/503
[58] Field of Search ........................ 564/493, 259, 503; 558/391, 446

[56] References Cited

U.S. PATENT DOCUMENTS 5,329,023  7/1994  Brussee et al. ...................... 564/493

Primary Examiner—Glennon H. Hollrah
Assistant Examiner—Scott C. Rand
Attorney, Agent, or Firm—Russel L. Brewer; William F. Marsh

[57] ABSTRACT

This invention relates to an improved process for the preparation of 3-aminopropanol and a primary amine by reacting a cyanoethyl ketoxime with hydrogen in the presence of a hydrogenation catalyst to generate the primary amine and aminopropanol. The sequence of reactions to form the aminopropanol and primary amine involves the reaction of hydroxylamine with a ketone to generate a ketoxime followed by reaction of acrylonitrile with the ketoxime to generate a cyanoethyl ketoxime followed by complete hydrogenation of the cyanoethyl ketoxime in the presence of a hydrogenation catalyst to generate the primary amine and aminopropanol. The significant advantage associated with this process is the high degree of selectivity to 3-aminopropanol and the primary amine.

8 Claims, No Drawings

PROCESS FOR PRODUCING AMINOPROPANOLS

FIELD OF THE INVENTION

This invention relates to a process for the coproduction of amino propanol and primary amines.

BACKGROUND OF THE INVENTION

3-Aminopropanol is used commercially for the production of panthenol and pantothenic acid and is produced by the catalyzed hydrogenation of 3-hydroxypropionitrile.

The most common route to 3-hydroxypropionitrile, the precursor of 3-aminopropanol, is the base catalyzed reaction of acrylonitrile with water. However, two by-product pathways reduce the selectivity of the reaction substantially. One pathway leads to hydrolysis of the nitrile functionality generating acrylamide and, under one set of operating conditions, acrylamide is by far the predominant product. Aside from reducing the selectivity to 3-hydroxypropionitrile, acrylamide is extremely difficult to separate from 3-hydroxypropionitrile as they codistill. At milder reaction conditions the formation of acrylamide is to some degree suppressed. But, a second pathway involves the reaction of 3-hydroxypropionitrile itself with acrylonitrile, thereby resulting in the formation of cyanoethyl ether. To alleviate cyanoethyl ether formation huge excesses of water are necessary to substantially suppress the amount of cyanoethyl ether formed. This, of course, leads to poor reactor productivity and expensive water removal methods.

Another route to 3-aminopropanol via 3-hydroxypropionitrile is through 2-chloroethanol. Sodium cyanide is reacted with 2-chloroethanol to produce 3-hydroxypropionitrile. 2-Chloroethanol and sodium cyanide are both highly toxic substances thereby create operational problems. In addition, 2-chloroethanol is corrosive and requires glass lined equipment.

The major problem associated with the above processes for producing hydroxypropionitrile lies in an inability to control selectivity of the reaction of acrylonitrile with water to enhance production of aminopropanol. Thus, the major obstacle in the 3-aminopropanol production process lies in the manufacture of 3-hydroxypropionitrile precursor. Methods practiced industrially to manufacture 3-hydroxypropionitrile are either chemically non-selective or involve the handling of highly corrosive and hazardous materials.

SUMMARY OF THE INVENTION

This invention relates to an improved process for the preparation of 3-aminopropanol and a primary amine by reacting a cyanoethyl ketoxime with hydrogen in the presence of a hydrogenation catalyst to generate the primary amine and aminopropanol. The sequence of reactions to form the aminopropanol and primary amine involves the reaction of hydroxylamine with a ketone to generate a ketoxime followed by reaction of acrylonitrile with the ketoxime to generate a cyanoethyl ketoxime followed by complete hydrogenation of the cyanoethyl ketoxime in the presence of a hydrogenation catalyst to generate the primary amine and aminopropanol. The significant advantage associated with this process is the high degree of selectivity to 3-aminopropanol and the primary amine.

DETAILED DESCRIPTION OF THE INVENTION

The general process for producing the primary amine and aminopropanol can be described in the following three sets of equations:

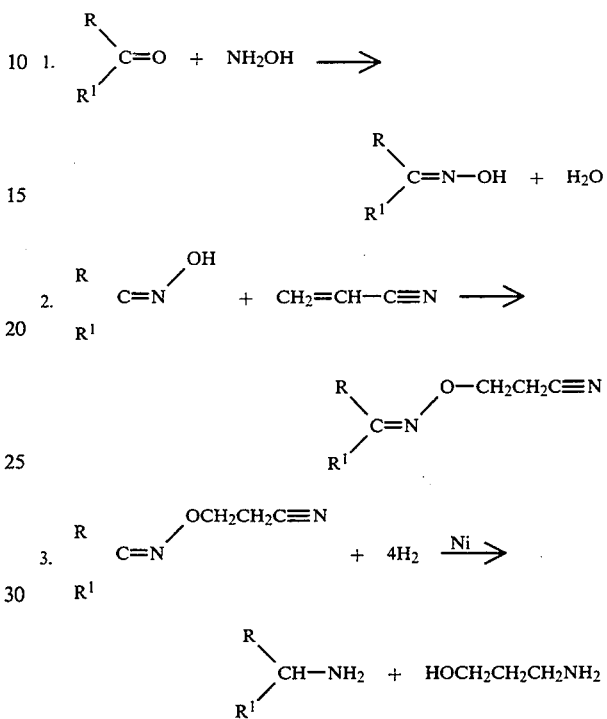

wherein R and R' are $C_1$-$C_8$ aliphatic or $C_{6-12}$ cycloaliphatic or aromatic components.

The ketones used in the above reaction with hydroxylamine can be virtually any organo ketone wherein R and R' are $C_2$-$C_8$ aliphatic, preferably alkyl groups, and $C_{6-12}$ cycloaliphatic and aromatic, and these include acetone, methylethylketone, diethylketone, methylisobutylketone, methylisopropylketone, etc.

The formation of the ketoxime is accomplished by reacting hydroxylamine with the ketone at a temperature of from about 25° to 75° C. and a pressure from about 1 to 3 bars in a stoichiometric ratio.

The addition of acrylonitrile to the ketoxime formed by the reaction of hydroxylamine with the ketone can be accomplished by reacting the ketoxime with acrylonitrile at a temperature of from 40° to 80° C. at a pressure of from 1 to 3 bars. Typically, a reaction time from 1 to 3 hours is required to complete the reaction.

The final reaction in the process involves the hydrogenation of the cyanoethyl ketoxime to 3-aminopropanol and the primary amine. It is believed there are four discrete hydrogenation steps involved in the hydrogenation of the cyanoethyl ketoxime to form aminopropanol and a primary amine. These steps include the cleavage of the N—O bond, the C=N saturation and the two-step conversion of the nitrile to the primary amine. Conditions for effecting reduction of the cyanoethyl ketoxime to the primary amine and to aminopropanol range from a temperature of from about 50° to 100° C. at hydrogen pressures of from 200 to 1500 psig. Hydrogenation times from 2 to 8 hours typically are required to effect hydrogenation.

Catalysts used for effecting hydrogenation of the cyanoethyl ketoxime to the primary amine and aminopropanol include conventional hydrogenation catalysts such as cobalt, nickel, palladium, platinum, and the like. Nickel is the catalyst of choice to effect the reduction of the cyanoethyl ketoxime.

The sequence by which the various hydrogenation steps described above occur is not absolutely known. Although not intending to be bound by theory, it is believed from the results obtained that either the N—O bond cleavage, or that the nitrile reduction precedes the C=N reduction. If in fact the opposite had occurred, it is believed that the driving force would lead to the formation of a five membered ring. The fact that this pathway is nonexistent or very minor is attested to by the very small amount of N-alkyl-3-aminopropanol that is obtained as shown in the experimental results. Thus, in fact, either the nitrile is completely reduced to the primary amine and/or the N—O is cleaved prior to the C=N reduction step.

The following examples are provided to illustrate various embodiments of the invention and are not intended to restrict the scope thereof.

Example 1

Generation of Methylisobutylketone Oxime (MIBK Oxime)

Into a 5-liter 4-necked round bottomed flask equipped with mechanical stirrer, reflux condenser, pressure equalizing dropping funnel and thermometer was placed 1500 g of water and 640 g (7.8 moles) of hydroxylamine sulfate. With stirring, 1350 ml of 25% aqueous sodium hydroxide was added and the solution then warmed to 40° C. with an external water bath. Over a period of 45 minutes, 601 g (6.0 moles) of methylisobutyl ketone (MIBK) was added from the dropping funnel. The two-phase reaction mixture was then cooled to 20° C., and the top organic layer was separated from the water phase. The crude MIBK oxime, 693 g, was found to contain 2.7 wt % water and was 99.54% pure by GC/FID.

Example 2

Generation of Cyanoethylated MIBK Oxime

Into a 2-liter four-necked round bottomed flask equipped with mechanical stirrer, reflux condenser, pressure-equalizing dropping funnel, and thermometer was placed 693 g of the MIBK oxime, without purification, from Example 1 and 6.16 g of Triton B (40 wt % N-benzyl-trimethylammonium hydroxide in methanol). This mixture was heated to 50° C. with an external water bath and then 350 g (6.6 moles) of acrylonitrile was added continuously over 35 minutes while stirring vigorously and maintaining the temperature between 50° and 60° C. An additional 1.54g of Triton B was added at this time and the reaction stirred at 55° C. an additional two hours. The crude product (1051 g) was neutralized with 0.41 g of 85% phosphoric acid and distilled through a short-path distillation apparatus to give 952 g of clear colorless liquid (bp 112° C. @ 10 torr). Analysis by GC/FID revealed the product to be 94.2 wt % cyanoethylated MIBK oxime and 1.45 wt % MIBK oxime. This represents an 89.0% yield of cyanoethylated MIBK oxime from the starting ketone and a 2.04% yield of MIBK oxime.

Example 3

Generation of 3-Aminopropanol and 1,3-Dimethylbutylamine

To a 1-liter stainless steel autoclave was added 21 g of chromium promoted sponge nickel catalyst and 300 g of water. The reactor was then purged several times with nitrogen and then hydrogen. With the reactor at atmospheric pressure, 46 g of anhydrous ammonia was charged into the reactor. The reactor contents were then heated to 70° C. and the pressure adjusted to 900 psig with hydrogen. The distilled cyanoethylated MIBK oxime from Example 2 was then pumped continuously into the reactor over a period of 3 hours. The reaction mass was allowed to stir an additional one hour to ensure complete uptake of hydrogen. The reaction was then allowed to cool and was vented to atmospheric pressure. The two-phase crude product was homogenized by agitation and a sample analyzed by GC/FID to be 63.3% 1,3-dimethylbutylamine and 28.2% 3-aminopropanol by weight.

What is claimed is:

1. In a process for the preparation of aminopropanol, the cyanoethylation of a hydroxyl-containing organic compound and the subsequent reduction of that nitrile group with hydrogen to produce aminopropanol, the improvement which comprises utilizing a cyanoethyl ketoxime represented by the formula:

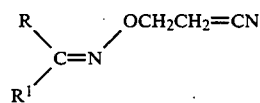

wherein R and R' are $C_1$–$C_8$ aliphatic or $C_{6-12}$ cycloaliphatic or aromatic component.

2. The process of claim 1 where R is $C_{1-8}$ aliphatic and the aliphatic group is an alkyl group.

3. The process of claim 1 wherein the hydrogenation catalyst used to effect reduction of the cyanoethyl ketoxime is nickel.

4. The process of claim 1 wherein the cyanoethylketoxime is methylisobutyloxime.

5. In a process for the production of aminopropanol, the improvement which comprises the steps:

a) reacting hydroxylamine with a a ketone in accordance with the reaction:

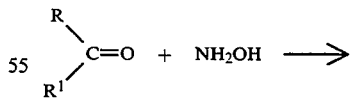

wherein R and R' are $C_1$–$C_8$ aliphatic or $C_{6-12}$ cycloaliphatic or aromatic components b) reacting the ketoxime produced in accordance with the reaction of step (a) with acrylonitrile to produce a cyanoethylated ketoxime in accordance with the formula:

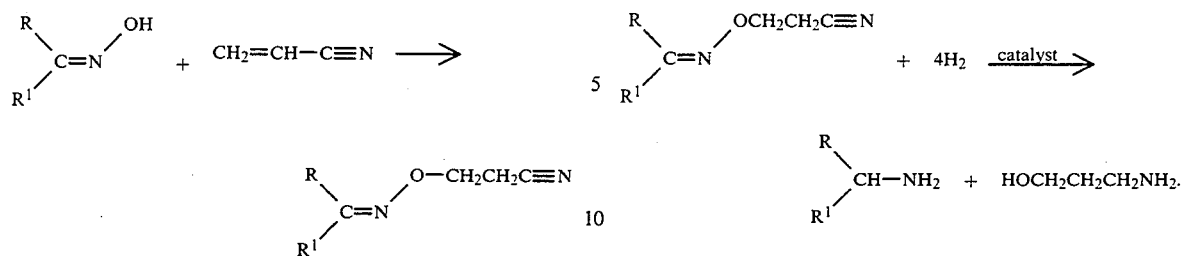

and then, (c) reacting the cyanoethyl ketoxime produced in accordance with step (b) with hydrogen to produce aminopropanolamine and a dialkyl substituted primary amine represented by the formula.

6. The process of claim 5 where R is $C_{1-8}$ aliphatic and the aliphatic group is an alkyl group.

7. The process of claim 6 wherein the catalyst used to effect hydrogenation and reduction of the cyanoethyl ketoxime in step (c) is nickel.

8. The process of claim 7 wherein the cyanoethylketoxime is methylisobutyloxime.

* * * * *